(12) United States Patent
Froissant et al.

(10) Patent No.: US 7,323,467 B2
(45) Date of Patent: Jan. 29, 2008

(54) 3-HETEROARYL-3,5-DIHYDRO-4-OXO-4H-PYRIDAZINO[4,5-B]INDOLE-1-ACETAMIDE DERIVATIVES, THEIR PREPARATION AND THEIR APPLICATION IN THERAPEUTICS

(75) Inventors: Jacques Froissant, Brevainville (FR); Benoit Marabout, Massy (FR); Frank Marguet, Verrieres le Buisson (FR); Frederic Puech, La Celle Saint Cloud (FR)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 11/749,342

(22) Filed: May 16, 2007

(65) Prior Publication Data

US 2007/0219202 A1 Sep. 20, 2007

Related U.S. Application Data

(63) Continuation of application No. 10/509,695, filed as application No. PCT/FR03/01027 on Apr. 2, 2003, now Pat. No. 7,235,554.

(30) Foreign Application Priority Data

Apr. 3, 2002 (FR) .................................. 02 04158

(51) Int. Cl.
*A61K 31/5025* (2006.01)
*A61P 25/02* (2006.01)
*A61P 25/16* (2006.01)

(52) U.S. Cl. ..................... 514/248; 514/232.8
(58) Field of Classification Search ............... 514/248, 514/232.8
See application file for complete search history.

(56) References Cited

U.S. PATENT DOCUMENTS 6,075,021 A   6/2000 Evanno et al.
6,262,045 B1  7/2001 Evanno et al.
6,395,729 B1  5/2002 Ferzaz et al.
7,109,194 B2  9/2006 Burnier et al.

FOREIGN PATENT DOCUMENTS

| WO | WO 98/15552 | 4/1998 |
|---|---|---|
| WO | WO 99/06406 | 2/1999 |
| WO | WO 00/44384 | 8/2000 |

OTHER PUBLICATIONS

Lacapere, J.J., et., al., Peripheral-Type Benzodiazepine Receptor: Structure and Function of a Cholesterol-Binding in Steroid and Bile Acid Biosynthesis, Steroids vol. 68, (2003) pp. 569-585.

*Primary Examiner*—Kahsay Habte
(74) *Attorney, Agent, or Firm*—Balaram Gupta

(57) ABSTRACT

The invention discloses and claims therapeutic uses of compounds of general formula (I)

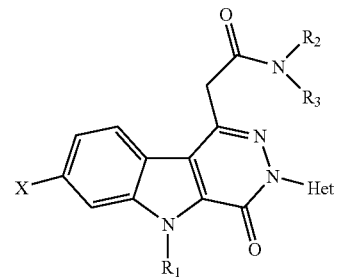

Wherein X, $R_1$, $R_2$ and $R_3$ are as described herein. The invention further discloses processes for preparing them, and novel intermediates therefor.

18 Claims, No Drawings

3-HETEROARYL-3,5-DIHYDRO-4-OXO-4H-PYRIDAZINO[4,5-B]INDOLE-1-ACETAMIDE DERIVATIVES, THEIR PREPARATION AND THEIR APPLICATION IN THERAPEUTICS

This application is a continuation of U.S. application Ser. No. 10/509,695, filed Sep. 30, 2004, now U.S. Pat. No. 7,235,554, which was the National Stage of International application No. PCT/FR03/01,027, filed Apr. 2, 2003, both of which are incorporated herein by reference in their entirety; which claims the benefit of priority of French Patent Application No. 02/04,158, filed Apr. 3, 2002.

The invention relates to 3-heteroaryl-3,5-dihydro-4-oxo-4H-pyridazino[4,5-b]indole-1-acetamide derivative compounds.

Already known are 3,5-dihydropyridazino[4,5-b]indole derivative compounds, described in document WO-A-0044384, which have in vitro affinity for peripheral benzodiazepine receptors (PBR or p sites). There still exists a need to find and to develop products which exhibit a good in vivo activity. The invention responds to this aim by providing new compounds which exhibit in vitro and in vivo affinity for peripheral benzodiazepine receptors.

The invention first provides the compounds of the general formula (I) below.

The invention also provides processes for preparing compounds of general formula (I).

The invention further provides compounds which can be used in particular as synthesis intermediates of compounds of general formula (I).

The invention additionally provides for uses of compounds of general formula (I) particularly in medicinal products or in pharmaceutical compositions.

The compounds of the invention are of the general formula (I):

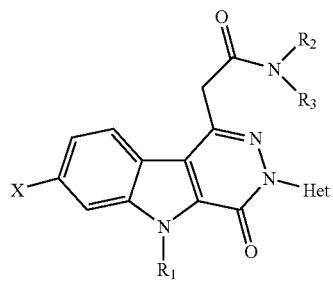

(I)

in which

X represents a hydrogen or halogen atom, $R_1$ represents a hydrogen atom or a $(C_1-C_4)$alkyl group, $R_2$ and $R_3$ each independently of one another represent a hydrogen atom or a $(C_1-C_4)$alkyl group, or else $R_2$ and $R_3$, together with the nitrogen atom bearing them, form a pyrrolidinyl, piperidinyl, morpholinyl or 4-$(C_1-C_4)$-alkylpiperazinyl group, and Het represents a heteroaromatic group of pyridinyl, quinolinyl, isoquinolinyl, pyrimidinyl, pyrazinyl or pyridazinyl type which may carry one or more halogen atoms and/or one or more $(C_1-C_4)$alkyl and/or $(C_1-C_4)$alkoxy groups.

The compounds of the invention may exist in the form of bases or addition salts with acids. Such addition salts form part of the invention.

These salts are advantageously prepared with pharmaceutically acceptable acids, although the salts of other acids useful, for example, for purifying or isolating compounds of formula (I) likewise form part of the invention.

The compounds of formula (I) may also exist in the form of hydrates or solvates; that is, in the form of associations or combinations with one or more molecules of water or with a solvent. Such hydrates and solvates likewise form part of the invention.

In the context of the present invention
- a halogen atom represents a fluorine, chlorine, bromine or iodine;
- a $(C_1-C_4)$alkyl group represents a linear or branched, saturated aliphatic group containing 1 to 4 carbon atoms. By way of example, mention may be made of methyl, ethyl, propyl, isopropyl, butyl, isobutyl and tert-butyl groups;
- a $(C_1-C_4)$alkoxy group represents an oxygen radical containing 1 to 4 carbon atoms which is substituted by an alkyl group as defined above.

Among the compounds of formula (I) provided by the invention, preferred compounds are the compounds for which
- X represents a halogen atom; and/or
- $R_1$ represents a $(C_1-C_4)$alkyl; and/or
- $R_2$ and $R_3$, each independently of one another, represent a $(C_1-C_4)$alkyl group, or else $R_2$ and $R_3$, together with the nitrogen atom bearing them, form a pyrrolidinyl or 4-$(C_1-C_4)$alkylpiperazinyl group; and/or
- Het represents a heteroaromatic group of pyridinyl type which may carry one or more halogen atoms and/or one or more $(C_1-C_4)$alkyl and/or $(C_1-C_4)$alkoxy groups.

Compounds for which X, $R_1$, $R_2$, $R_3$ and Het are all as defined above in the subgroups of preferred compounds are particularly preferred, and more specifically, among these, the compounds for which X represents a chlorine atom, $R_1$ represents a methyl group.

Among the compounds of formula (I) provided by the invention, by way of example, compounds of the invention are the following:

1: 7-fluoro-N,N,5-trimethyl-4-oxo-3-(pyridin-2-yl)-3,5-dihydro-4H-pyridazino[4,5-b]indole-1-acetamide 2: 7-fluoro-N,N,5-trimethyl-4-oxo-3-(pyridin-3-yl)-3,5-dihydro-4H-pyridazino[4,5-b]indole-1-acetamide hydrochloride (1:1)

3: 7-fluoro-N,N,5-trimethyl-4-oxo-3-(pyridin-4-yl)-3,5-dihydro-4H-pyridazino[4,5-b]indole-1-acetamide hydrochloride (1:1)

4: 7-chloro-N,N,5-trimethyl-4-oxo-3-(pyridin-2-yl)-3,5-dihydro-4H-pyridazino[4,5-b]indole-1-acetamide 5: 7-chloro-N,N,5-trimethyl-4-oxo-3-(pyridin-3-yl)-3,5-dihydro-4H-pyridazino[4,5-b]indole-1-acetamide 6: 7-chloro-N,N,5-trimethyl-4-oxo-3-(pyridin-3-yl)-3,5-dihydro-4H-pyridazino[4,5-b]indole-1-acetamide hydrochloride (1:1)

7: 7-chloro-N,N, 5-trimethyl-4-oxo-3-(pyridin-4-yl)-3,5-dihydro-4H-pyridazino[4,5-b]indole-1-acetamide hydrochloride (1:1)

8: 7-chloro-N,N,5-trimethyl-4-oxo-3-(6-methylpyridin-3-yl)-3,5-dihydro-4H-pyridazino[4,5-b]indole-1-acetamide 9: 7-chloro-N,N-diethyl-5-methyl-4-oxo-3-(pyridin-3-yl)-3,5-dihydro-4H-pyridazino[4,5-b]indole-1-acetamide 10  4-methyl-1-[2-[7-chloro-5-methyl-3-(pyridin-3-yl)-4-oxo-3,5-dihydro-4H-pyridazino[4,5-b]indol-1-yl]acet-1-yl]piperazine hydrochloride (1:1)

11: 1-[2-[7-chloro-5-methyl-3-(pyridin-3-yl)-4-oxo-3,5-dihydro-4H-pyridazino[4,5-b]indol-1-yl]acet-1-yl]pyrrolidine 12  1-[2-[7-chloro-5-methyl-3-(pyridin-4-yl)-4-oxo-3,5-dihydro-4H-pyridazino[4,5-b]indol-1-yl]acet-1-yl]pyrrolidine hydrochloride (1:1)

The compounds of general formula (I) can be prepared by processes which are illustrated hereinbelow.

Throughout the remainder of the description the intermediate compounds (II), (III), (IV) and (V) are those shown in the scheme below.

Scheme

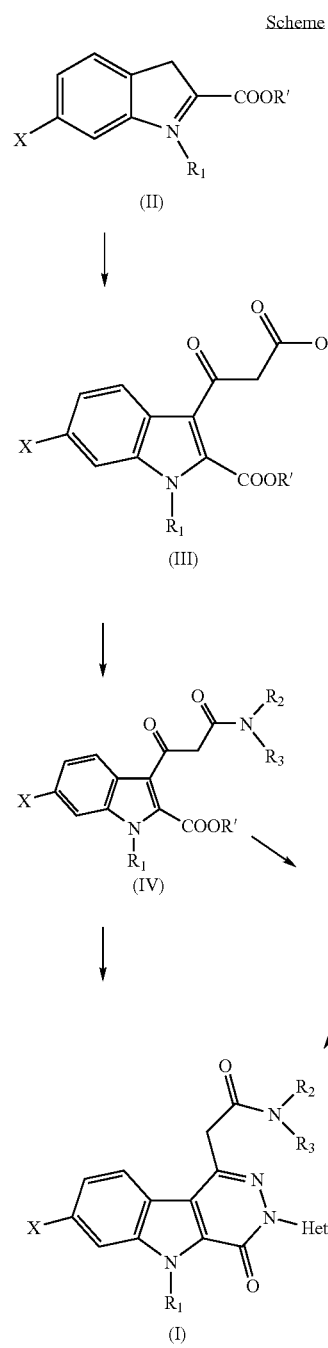

A compound of general formula (II) in which X and $R_1$ are as defined above and R' represents a $(C_1-C_4)$alkyl group is treated with a 3-chloro-3-oxopropanoate of general formula $ClCOCH_2CO_2R''$, in which R'' represents a $(C_1-C_4)$alkyl group, in a solvent such as dichloroethane at ambient temperature in the presence of a Lewis acid, titanium tetrachloride for example, to give the diester of general formula (III).

The keto ester function of the diester of general formula (III) is converted into keto amide to give the compound of general formula (IV) by the action of an amine of general formula $HNR_2R_3$, in which $R_2$ and $R_3$ are as defined above, in the presence of a catalyst such as 4-(dimethylamino)pyridine.

According to a first preparation pathway the compound of general formula (IV) is treated in a polar solvent in the presence of acid with a heteroarylhydrazine to give an amide of general formula (I).

According to a second preparation pathway the compound of general formula (IV) is treated with hydrazine with heating in a solvent such as toluene in the presence of a catalytic amount of acid to give a pyridazinoindole of general formula (V). Finally an N-arylation reaction is performed on the pyridazinoindole of general formula (V) in the presence of a heteroaryl halide, or else of a heteroarylboronic acid derivative and a metal salt, such as a copper salt, leading to a compound of general formula (I).

The reactants employed above are available commercially or are described in the literature, or else can be prepared by methods which are described therein or which are known to the skilled worker.

More particularly the boronic acid derivatives bearing a heteroaromatic group may be prepared by methods analogous to those known in the literature (*Synth. Commun.* 1996, 26, 3543 and WO9803484).

The preparation of the starting compounds of general formula (II) is described in the document WO-A-0044751 in the case where X is a chlorine atom. In the case where X is a fluorine atom the compound of general formula (II) is prepared analogously starting from methyl 6-fluoroindole-2-carboxylate, which is described in the literature (*J. Med. Chem.* 2000, 43, 4701).

The invention also provides the compounds of general formula (III),

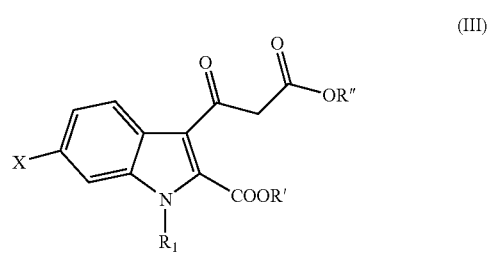

in which
X represents a hydrogen or halogen atom,
$R_1$ represents a hydrogen atom or a $(C_1-C_4)$alkyl group,
R' and R'', each independently of one another, represent a $(C_1-C_4)$alkyl group,
which are useful as synthesis intermediates for preparing compounds of general formula (I).

The invention additionally provides the compounds of general formula (IV),

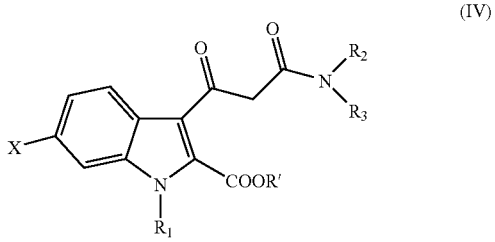

(IV)

in which
X represents a hydrogen or halogen atom,
R₁ represents a hydrogen atom or a (C₁-C₄)alkyl group,
R' represents a (C₁-C₄)alkyl group,
R₂ and R₃, each independently of one another, represent a hydrogen atom or a (C₁-C₄)alkyl group, or else R₂ and R₃, together with the nitrogen atom bearing them, form a pyrrolidinyl, piperidinyl, morpholinyl or 4-(C₁-C₄)alkylpiperazinyl group,
which are useful as synthesis intermediates for preparing compounds of general formula (I).

The invention further provides the compounds of general formula (V)

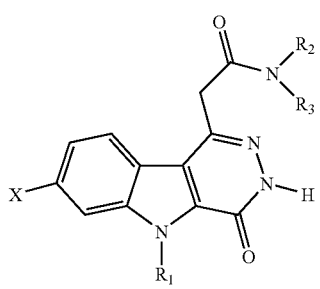

(V)

in which
X represents a hydrogen or halogen atom,
R₁ represents a hydrogen atom or a (C₁-C₄) alkyl group,
R₂ and R₃, each independently of one another, represent a hydrogen atom or a (C₁-C₄)alkyl group, or else R₂ and R₃, together with the nitrogen atom bearing them, form a pyrrolidinyl, piperidinyl, morpholinyl or 4-(C₁-C₄) alkylpiperazinyl group,
which are useful as synthesis intermediates for preparing compounds of general formula (I).

The examples about to follow illustrate the preparation of some compounds of the invention. These examples are not limitative and only illustrate the invention. The numbers of the compounds exemplified tie up with those given in the table thereafter, which illustrates the chemical structures and the physical properties of some compounds in accordance with the invention. The elemental microanalyses and the IR and NMR spectra confirm the structures of the compounds obtained.

EXAMPLE 1

Compound 1

7-fluoro-N,N,5-trimethyl-4-oxo-3-(pyridin-2-yl)-3,5-dihydro-4H-pyridazino[4,5-b]indole-1-acetamide 1.1. Methyl 6-fluoro-1-methyl-1H-indole-2-carboxylate A 60% suspension of 7.9 g (197 mmol) of sodium hydride (washed with petroleum ether beforehand) and 36.1 g (176 mmol) of methyl 6-fluoro-1H-indole-2-carboxylate (containing 10 to 20% of ethyl 6-fluoro-1H-indole-2-carboxylate) in 250 ml of N,N-dimethylformamide is stirred at ambient temperature for 2 h. Then 12 ml (193 mmol) of iodomethane in 50 ml of N,N-dimethylformamide are added and the mixture is stirred at ambient temperature for 12 h.

The contents are poured into an ice/water mixture. Dichloromethane is added and the aqueous phase is neutralized with hydrochloric acid (1N). The organic phase is separated off, washed with water, dried over sodium sulfate, filtered and concentrated under reduced pressure. The residue is purified by chromatography on a silica gel column in a mixture of solvents (cyclohexane/dichloromethane: 50/50 to 0/100 then dichloromethane/ethyl acetate: 100/0 to 70/30).

32.7 g (170 mmol) are isolated of a white compound of methyl 6-fluoro-1-methyl-1H-indole-2-carboxylate containing 10 to 20% of ethyl 6-fluoro-1-methyl-1H-indole-2-carboxylate.

1.2. methyl 3-[6-fluoro-2-(methoxycarbonyl)-1-methyl-1H-indol-3-yl]-3-oxopropanoate In portions, 6.5 ml (60 mmol) of methyl 3-chloro-3-oxopropanoate are added to a solution of 6.6 ml (60 mmol) of titanium tetrachloride in 80 ml of 1,2-dichloroethane. The mixture is stirred at ambient temperature for 30 minutes. A solution of 5 g (24.1 mmol) of methyl 6-fluoro-1-methyl-1H-indole-2-carboxylate (containing 10 to 20% of ethyl 6-fluoro-1-methyl-1H-indole-2-carboxylate), obtained in step 1.1., is added and the mixture is stirred at 40° C. for 20 h. The mixture is poured into ice water and extracted with dichloromethane. The organic phase is separated off, washed with water, dried over sodium sulfate, filtered and concentrated under reduced pressure. The residue is purified by chromatography on a silica gel column (eluent: cyclohexane/dichloromethane: 90/10 to 0/100 then dichloromethane/ethyl acetate 100/0 to 50/50). This gives 13 g of a pasty solid containing primarily the compound. It is used as it is in the rest of the synthesis.

1.3 N,N-dimethyl-3-[6-fluoro-2-(methoxycarbonyl)-1-methyl-1H-indol-3-yl]-3-oxopropanamide A stream of gaseous dimethylamine is passed into a mixture of 13 g (44.4 mmol) of methyl 3-[6-fluoro-2-(methoxycarbonyl)-1-methyl-1H-indol-3-yl]-3-oxo-propanoate, obtained in step 1.2., and 0.2 g (1.63 mmol) of 4-(N,N-dimethyl)aminopyridine in 80 ml of toluene. Immediately a condenser, surmounted by a balloon flask, is fitted and the solution is stirred at 100° C. for 20 h. The mixture is cooled to ambient temperature and concentrated under reduced pressure. 200 ml of dichloromethane, water and hydrochloric acid (1N) are added. The organic phase is separated off, washed with water, dried over sodium sulfate, filtered and concentrated under reduced pressure. The residue is purified by chromatography on a silica gel column (eluent: cyclohexane/dichloromethane: 50/50, then dichloromethane/ethyl acetate 100/0 to 0/100).

4.6 g (14 mmol) are isolated of a yellow solid, which is used as it is in the rest of the synthesis.

1.4 7-fluoro-N,N,5-trimethyl-4-oxo-3-(pyrid-2-yl)-3,5-dihydro-4H-pyridazino[4,5-b]indole-1-acetamide A solution of 1.4 g (4.1 mmol) of N,N-dimethyl-3-[6-fluoro-2-(methoxycarbonyl)-1-methyl-1H-indol-3-yl]-3-oxopropanamide, obtained in step 1.3., in 40 ml of absolute ethanol is heated at reflux for 22 h with a few drops of glacial acetic acid and 1.4 g (12.8 mmol) of 2-pyridylhydrazine.

The mixture is cooled and concentrated under reduced pressure. Water and 200 ml of dichloromethane are added. Sodium hydroxide solution is added to a pH>10. The organic phase is separated off, washed with water, dried over sodium sulfate, filtered and concentrated under reduced pressure. The residue is purified by chromatography on a silica gel column in a mixture of solvents (dichloromethane/ethyl acetate: 100/0 to 0/100, then ethyl acetate/methanol: 100/0 to 90/10). The product obtained is subsequently chromatographed on a neutral alumina column in a mixture of solvents (dichloromethane/ethyl acetate: 100/0 to 0/100, then ethyl acetate/methanol: 100/0 to 90/10). This gives a solid, which is rinsed with diethyl ether.

0.25 g (0.66 mmol) of compound is isolated in the form of a white solid.

Melting point: 222-223° C.; M+H$^+$: 380.

EXAMPLE 2

Compound 6

7-chloro-N,N,5-trimethyl-4-oxo-3-(pyridin-3-yl)-3,5-dihydro-4H-pyridazino[4,5-b]indole-1-acetamide hydrochloride 2.1 ethyl 3-[6-chloro-2-(methoxycarbonyl)-1-methyl-1H-indol-3-yl]-3-oxopropanoate A solution of 6.2 ml (48.4 mmol) of ethyl 3-chloro-3-oxopropanoate in 70 ml of 1,2-dichloroethane is cooled to 0° C. In small portions 5.3 ml (48.3 mmol) of titanium tetrachloride are added and the mixture is stirred at 0° C. for 30 minutes. A solution of 4.3 g (19.2 mmol) of methyl 6-chloro-1-methyl-1H-indole-2-carboxylate in 35 ml of 1,2-dichloroethane is added and the mixture is stirred at ambient temperature for 12 h. It is poured into ice water and extracted with dichloromethane. The organic phase is separated off, washed with water, dried over sodium sulfate, filtered and concentrated under reduced pressure. The residue is purified by chromatography on a silica gel column (eluent: cyclohexane/ethyl acetate: 90/10 to 80/20). This gives a yellow solid, which is triturated in heptane and then in diisopropyl ether.

2.84 g (8.4 mmol) of compound are recovered, in the form of a cream-colored solid.

2.2 3-[6-chloro-2-(methoxycarbonyl)-1-methyl-1H-indol-3-yl]-N,N-dimethyl-3-oxopropanamide A stream of gaseous dimethylamine is passed into a mixture of 15 g (44.4 mmol) of ethyl 3-[6-chloro-2-(methoxycarbonyl)-1-methyl-1H-indol-3-yl]-3-oxo-propanoate, obtained in step 2.1., and 0.2 g (1.63 mmol) of 4-(N,N-dimethyl)aminopyridine in 100 ml of toluene. Immediately a condenser, surmounted by a balloon flask, is fitted and the solution is stirred at 100° C. under low pressure for 20 h. The mixture is cooled to ambient temperature and concentrated under reduced pressure and the residue is chromatographed on a silica gel column (eluent: cyclohexane/dichloromethane: 50/50, then dichloromethane/ethyl acetate: 100/0 to 0/100). This gives 3.8 g of a yellow solid which is recrystallized from a dichloromethane/ethyl acetate mixture.

1.8 g (5.3 mmol) are isolated of a yellow-white solid.

2.3 7-chloro-N,N,5-trimethyl-4-oxo-3,5-dihydro-4H-pyridazino[4,5-b]indole-1-acetamide A solution of 1.7 g (5.2 mmol) of 3-[6-chloro-2-(methoxycarbonyl)-1-methyl-1H-indol-3-yl]-N,N-dimethyl-3-oxopropanamide, obtained in step 2.2., in 150 ml of toluene is heated at 90° C. for 24 h in the presence of 1.8 ml (36.8 mmol) of hydrazine monohydrate and a catalytic amount of p-toluenesulfonic acid.

The mixture is cooled, an insoluble product is collected by filtration and is washed with water and then with diisopropyl ether and dried under reduced pressure.

1.70 g (5.2 mmol) of compound are isolated, in the form of a white solid.

Melting point: >300° C.

2.4 7-chloro-N,N,5-trimethyl-4-oxo-3-(pyridin-3-yl)-3,5-dihydro-4H-pyridazino[4,5-b]indole-1-acetamide hydrochloride 0.2 g (0.63 mmol) of 7-chloro-N,N,5-trimethyl-4-oxo-3,5-dihydro-4H-pyridazino[4,5-b]indole-1-acetamide, obtained in step 2.3., is dissolved in 15 ml of N-methylpyrrolidone. At ambient temperature and under an argon atmosphere 0.11 ml (1.4 mmol) of pyridine, 0.19 ml (1.4 mmol) of triethylamine, 1 g of molecular sieve, 0.24 g (1.3 mmol) of cupric acetate and 0.22 g (1.4 mmol) of 2-(pyridin-3-yl)-1,3,2-dioxaborinane are introduced. After 24 h of reaction the insoluble fractions are removed by filtration and the solution is admixed with 0.11 ml (1.4 mmol) of pyridine, 0.19 ml (1.4 mmol) or triethylamine, 1 g of molecular sieve, 0.24 g (1.3 mmol) of cupric acetate and 0.22 g (1.4 mmol) of 2-(pyridin-3-yl)-1,3,2-dioxaborinane. The reaction is stirred for a further 24 h. The insoluble fractions are removed by filtration and the filtrate is concentrated under reduced pressure to remove the solvent. Dichloromethane and water are added. The aqueous phase is extracted with dichloromethane. The organic phases are combined and washed with water. They are dried over sodium sulfate, filtered and concentrated under reduced pressure. The residue is purified by chromatography on a silica gel column (eluent: dichloromethane, then ethyl acetate/methanol: 100/0 to 80/20). A solid is obtained which is dissolved in a dichloromethane/methanol mixture. Ethyl acetate is added and the mixture is partly concentrated. A solid is isolated by filtration and is recrystallized from a mixture of ethanol and dichloromethane. 110 mg of 7-chloro-N,N,5-trimethyl-4-oxo-3-(pyridin-3-yl)-3,5-dihydro-4H-pyridazino[4,5-b]indole-1-acetamide (Compound 5) are recovered, in the form of a white solid.

Melting point: 255-256° C.

The hydrochloride is formed by dissolving the solid isolated above in a mixture of methanol and dichloromethane and by adding a 5N solution of hydrochloric acid in propan-2-ol. After recrystallization from ethanol, 0.09 g (0.20 mmol) of compound is isolated, in the form of a white solid.

Melting point: 250-252° C.: M+H$^+$: 396.

EXAMPLE 3

Compound 10

4-methyl-1-[2-[7-chloro-5-methyl-4-oxo-3-(pyridin-3-yl)-3,5-dihydro-4H-pyridazino[4,5-b]indol-1-yl] acet-1-yl]piperazine hydrochloride (1:1)

3.1. [3-(6-chloro-2-methoxycarbonyl)-1-methyl-1H-indol-3-yl]-3-oxopropion-1-yl]-4-methylpiperazine A solution of 2.84 g (8.4 mmol) of ethyl 3-[6-chloro-2-(methoxycarbonyl)-1-methyl-1H-indol-3-yl]-3-oxopropanoate, obtained in step 2.1. of example 2, in 160 ml of toluene is heated at reflux for 12 h in the presence of 3.7 ml (34 mmol) of N-methylpiperazine and 110 mg (0.9 mmol) of 4-(N,N-dimethylamino)pyridine.

The mixture is cooled to ambient temperature. 100 ml of dichloromethane, 80 ml of water and 10 ml of 20% aqueous ammonia are added. The organic phase is separated off, the aqueous phase is extracted with dichloromethane (2 times 100 ml) and the organic phases are combined. They are washed with water, dried over sodium sulfate, filtered and concentrated under reduced pressure and the residue is purified by chromatography on a silica gel column (eluent: dichloromethane/methanol: 100/0 to 90/10). This gives 1.68 g (4.3 mmol) of a yellow oil.

3.2. 4-methyl-1-[2-[7-chloro-5-methyl-4-oxo-3,5-dihydro-4H-pyridazino[4,5-b]indol-1-yl]acet-1-yl]piperazine A solution of 1.68 g (4.3 mmol) of [3-[6-chloro-2-(methoxycarbonyl)-1-methyl-1H-indol-3-yl]-3-oxopropion-1-yl]-4-methylpiperazine, obtained in step 3.1., in 80 ml of toluene is heated at 90° C. for 24 h in the presence of 1.7 ml (35 mmol) of hydrazine monohydrate and a catalytic amount of p-toluenesulfonic acid.

The mixture is cooled, and the insoluble fraction is collected by filtration and washed with water and then with diisopropyl ether and is dried under reduced pressure.

1.43 g (3.8 mmol) of compound are isolated, in the form of a white solid.

Melting point: >300° C.

3.3. 4-methyl-1-[2-[7-chloro-5-methyl-4-oxo-3-(pyridin-3-yl)-3,5-dihydro-4H-pyridazino[4,5-b]indol-1-yl)acet-1-yl]piperazine hydrochloride (1:1)

0.45 g (1.2 mmol) of 4-methyl-1-[2-[7-chloro-5-methyl-4-oxo-3,5-dihydro-4H-pyridazino[4,5-b]indol-1-yl)acet-1-yl]piperazine, obtained in step 3.2., is dissolved in 30 ml of N-methylpyrrolidone. At ambient temperature and under an argon atmosphere 0.2 ml (2.4 mmol) of pyridine, 0.34 ml (2.4 mmol) of triethylamine, 0.30 g of molecular sieve, 0.44 g (2.4 mmol) of cupric acetate and 0.39 g (2.4 mmol) of 2-(pyridin-3-yl)-1,3,2-dioxaborinane are introduced. After 24 h of reaction the insoluble fractions are removed by filtration and 0.2 ml (2.4 mmol) of pyridine, 0.34 ml (2.4 mmol) or triethylamine, 0.30 g of molecular sieve, 0.44 g (2.4 mmol) of cupric acetate and 0.39 g (2.4 mmol) of 2-(pyridin-3-yl)-1,3,2-dioxaborinane are added to the solution. The reaction is stirred for a further 24 h. The insoluble fractions are removed by filtration and the filtrate is concentrated under reduced pressure to remove the solvent. Dichloromethane and water are added. The aqueous phase is extracted with dichloromethane. The organic phases are combined and washed with water. They are dried over sodium sulfate and concentrated under reduced pressure. The residue is purified by chromatography on a silica gel column (eluent: dichloromethane/methanol: 100/0 to 90/10).

A white solid is recovered, whose hydrochloride is formed by dissolving it in a mixture of propan-2-ol and methanol and by adding a 0.1 N solution of hydrochloric acid in propan-2-ol. After recrystallization from a mixture of propan-2-ol and methanol, 0.34 g (0.70 mmol) of compound is isolated, in the form of a white solid.

Melting point: 287° C. (decomposition); M+H$^+$: 451.

EXAMPLE 4

Compound 8

7-chloro-N,N,5-trimethyl-4-oxo-3-(6-methylpyridin-3-yl)-3,5-dihydro-4H-pyridazino[4,5-b]indole-1-acetamide 0.4 g (1.25 mmol) of 7-chloro-N,N,5-trimethyl-4-oxo-3,5-dihydro-4H-pyridazino[4,5-b]indole-1-acetamide, obtained in step 2.3. of example 2, is dissolved in 45 ml of N-methylpyrrolidone. At ambient temperature and under an argon atmosphere, 0.2 ml (2.5 mmol) of pyridine, 0.35 ml (2.5 mmol) of triethylamine, 0.40 g of molecular sieve, 0.45 g (2.5 mmol) of cupric acetate and 0.80 g (3.6 mmol) of 4,4,5,5-tetramethyl-2-(6-methylpyridin-3-yl)-1,3,2-dioxaborolane are introduced. After 24 h of reaction 0.2 ml (2.5 mmol) of pyridine, 0.35 ml (2.5 mmol) of triethylamine, 0.40 g of molecular sieve, 0.45 g (2.5 mmol) of cupric acetate and 0.80 g (3.6 mmol) of 4,4,5,5-tetramethyl-2-(6-methylpyridin-3-yl)-1,3,2-dioxaborolane are added to the solution. The reaction is stirred for a further 24 h. The insoluble fractions are removed by filtration and the filtrate is concentrated under reduced pressure to remove the solvent. Dichloromethane and water are added. The aqueous phase is extracted with dichloromethane. The organic phases are combined and washed with water. They are dried over sodium sulfate, filtered and concentrated under reduced pressure. The residue is purified by chromatography on a silica gel column (eluent: dichloromethane/methanol: 100/0 to 80/20). This gives a solid, which is recrystallized from an isopropanol/methanol mixture.

0.12 g (0.29 mmol) of compound is isolated, in the form of a white solid.

Melting point: 253-255° C.; M+H$^+$: 410.

The table below illustrates the chemical structures and physical properties of some compounds of the invention.

In the "Salt" column of these tables, "HCl" denotes a hydrochloride, "–" denotes a compound in base form. The acid:base molar ratios are indicated opposite. The abbreviation dec. signifies that at the temperature given the solid is in the state of decomposition.

TABLE

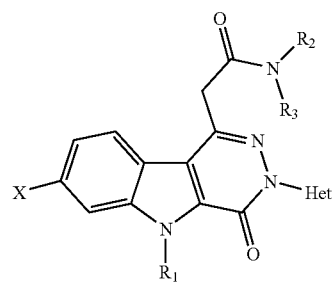

(I)

| Compound | X | $R_1$ | $NR_2R_3$ | Het | Salt | m.p. (° C.) |
|---|---|---|---|---|---|---|
| 1 | F | $CH_3$ | $N(CH_3)_2$ | pyridin-2-yl | — | 222-223 |
| 2 | F | $CH_3$ | $N(CH_3)_2$ | pyridin-3-yl | HCl 1:1 | 244-250 |
| 3 | F | $CH_3$ | $N(CH_3)_2$ | pyridin-4-yl | HCl 1:1 | 267-270 |

TABLE-continued (I)

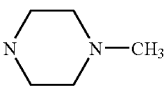

| Compound | X | $R_1$ | $NR_2R_3$ | Het | Salt | m.p. (° C.) |
|---|---|---|---|---|---|---|
| 4 | Cl | $CH_3$ | $N(CH_3)_2$ | pyridin-2-yl | — | 183-184 |
| 5 | Cl | $CH_3$ | $N(CH_3)_2$ | pyridin-3-yl | — | 255-256 |
| 6 | Cl | $CH_3$ | $N(CH_3)_2$ | pyridin-3-yl | HCl 1:1 | 250-252 |
| 7 | Cl | $CH_3$ | $N(CH_3)_2$ | pyridin-4-yl | HCl 1:1 | 275-279 |
| 8 | Cl | $CH_3$ | $N(CH_3)_2$ | 6-methyl-pyridin-3-yl | — | 253-255 |
| 9 | Cl | $CH_3$ | $N(CH_2CH_3)_2$ | pyridin-3-yl | — | 199-200 |
| 10 | Cl | $CH_3$ |  | pyridin-3-yl | HCl 1:1 | 287 (dec.) |
| 11 | Cl | $CH_3$ |  | pyridin-3-yl | — | 267-268 |
| 12 | Cl | $CH_3$ |  | pyridin-4-yl | HCl 1:1 | 248-251 |

The compounds of the invention formed the object of pharmacological tests which demonstrated their advantage as substances with therapeutic activities.

The compounds of the invention also exhibit characteristics of solubility in water, which promote effective in vivo activity.

Study of [³H]Ro5-4864 Binding to Peripheral benzodiazepine Receptors (PBR or p sites).

The affinity of the compounds of the invention for PBR or p sites (peripheral-type binding sites on benzodiazepines) was determined.

The p site receptors can be labeled selectively in rat kidney membranes incubated in the presence of [³H]Ro5-4864. The compounds of the invention formed the object of an in vitro study with respect to their affinity for these receptors.

The animals used are male Sprague-Dawley rats (Iffa Credo) weighing 180 to 300 mg. Following decapitation, the kidney is removed and the tissue is homogenized at 4° C. using a Polytron™ homogenizer for 2 min at 6/10 of the maximum speed in 35 volumes of 50 mM $Na_2HPO_4$ phosphate buffer at a pH adjusted to 7.5 with $NaH_2PO_4$. The membrane homogenate is filtered through gauze and diluted 10 times with the buffer.

[³H]Ro5-4864 (specific activity: 70-90 Ci/mmol; New England Nuclear) at a concentration of 0.5 nM is incubated in the presence of 100 μl of membrane homogenate in a final volume of 1 ml of buffer containing the test compound.

After incubation at 0° C. for 3 h the membranes are recovered by filtration on Whatman GF/B™ filters washed with 2 times 4.5 ml of cold (0° C.) incubation buffer. The amount of radioactivity retained by the filter is measured by liquid scintigraphy.

For each concentration of compound studied, the percentage inhibition of the binding of [³H]Ro5-4864, and then the $IC_{50}$ concentration, the concentration which inhibits 50% of the specific binding, are determined. The $IC_{50}$ values of the best compounds of the invention range from 1 nM to 200 nM.

The compounds of the invention are therefore ligands with affinity for peripheral benzodiazepine receptors.

Study of Neurotropic Activity.

Tests of Survival of Motor Neurons Following Section of the Facial Nerve in 4-day-old Rats After lesion of the facial nerve in the immature rat, the motor neurons of the facial nucleus suffer neuronal death by apoptosis. Neuronal survival is evaluated by means of histological and neuronal counting methods. Immature rats 4 days old are anesthetized with pentobarbital (3 mg/kg i.p.). The right facial nerve is exposed and sectioned, at its outlet from the stylomastoid foramen. After waking, the young rats are returned to their mother and treated for 7 days, with one or two administrations daily, orally or intraperitoneally, at doses ranging from 1 to 10 mg/kg. 7 days after the lesion, the animals are decapitated and the brains are frozen in isopentane at −40° C. The facial nucleus is cut with a cryostat into 10 μm sections, in its entirety. The motor neurons are stained with cresyl violet and counted using the Histo™ software (Biocom™).

In this model the compounds of the invention increased neuronal survival by approximately 10 to 30%.

The results of the tests show that compounds of the invention promote nerve regeneration.

The compounds according to the invention can therefore be used for preparing medicinal products.

Thus according to another of its aspects the invention provides medicinal products which comprise a compound of formula (I) or an addition salt thereof with a pharmaceutically acceptable acid or else a hydrate or a solvate of the compound of formula (I).

These medicinal products find their application in therapeutics, particularly for the prevention and/or treatment of peripheral neuropathies of various types, such as traumatic or ischemic neuropathies, infectious, alcoholic, medicinal or genetic neuropathies, and motor neuron conditions, such as spinal amyotrophies and amyotrophic lateral sclerosis. These medicinal products will also find application in the treatment of neurodegenerative diseases of the central nervous system, either of acute type, such as cerebral vascular accidents and cranial and medullar traumas, or of chronic type, such as autoimmune diseases (multiple sclerosis), Alzheimer's disease, Parkinson's disease and any other disease in which the administration of neurotrophic factors is supposed to have a therapeutic effect.

The compounds according to the invention can also be used in the treatment of acute or chronic renal insufficiency, glomerulonephritis, diabetic nephropathy, cardiac ischemia and cardiac insufficiency, myocardial infarction, ischemia of the lower limbs, coronary vasospasm, angina pectoris, pathologies associated with the heart valves, inflammatory heart diseases, side effects due to cardiotoxic medicaments or following cardiac surgery, atherosclerosis and its thromboembolic complications, restenosis, graft rejections, or ailments linked to incorrect proliferation or incorrect migration of the smooth muscle cells.

Furthermore, recent data in the literature indicate that the peripheral benzodiazepine receptor might play a fundamental part in the regulation of cell proliferation and cancerization processes. Generally, and in comparison with normal tissues, an increased density of peripheral benzodiazepine receptors is observed in various types of tumors and cancers.

In human astocytomas the degree of expression of the peripheral benzodiazepine receptor is correlated with the degree of malignancy of the tumor, the proliferation index and the survival of the patients. In human cerebral tumors the increase in the number of peripheral benzodiazepine receptors is used as a diagnostic indication in medical imaging and as a therapeutic target for conjugates formed from a ligand of the peripheral benzodiazepine receptor and a cytostatic drug. A high density of peripheral benzodiazepine receptors is also observed in ovarian carcinomas and breast cancers. As regards the latter, it has been demonstrated that the degree of expression of the peripheral benzodiazepine receptors is related to the aggression potential of the tumor; moreover, the presence of a peripheral benzodiazepine receptor agonist stimulates the growth of a mammary cancer line.

The entirety of these results, which suggests a deleterious function of the peripheral benzodiazepine receptor in cancerization processes, constitutes a relevant basis for the search for synthetic ligands specific to the peripheral benzodiazepine receptor which are capable of blocking its effects.

The compounds can therefore be used for treating tumors and cancers.

Peripheral benzodiazepine receptors are also present in the skin and, in this respect, the compounds which can be used according to the invention can be used for the prophylaxis or treatment of cutaneous stresses.

By cutaneous stresses are meant the various situations which could cause damage, in particular to the epidermis, irrespective of the agent causing this stress. That agent may be internal and/or external to the body, such as a chemical or free-radical agent, or else external, such as ultraviolet radiation. Accordingly the compounds which can be used according to the invention are intended for preventing and combating skin irritation, dry patches, erythemas, disesthesic sensations, heating sensations, pruritus of the skin and/or of the mucosae, or ageing, and can also be used in skin disorders such as, for example, psoriasis, pruriginous diseases, herpes, photodermatoses, atopic dermatites, contact dermatites, lichens, prurigos, insect stings, in fibroses and other collagen maturation disorders, in immunological disorders or else in dermatological conditions, such as eczema.

The compounds of the invention can also be used for preventing and treating chronic inflammatory diseases, especially rheumatoid arthritis.

According to another of its aspects the invention provides pharmaceutical compositions comprising as active principle at least one compound of general formula (I). These pharmaceutical compositions comprise an effective dose of at least one compound of the invention, in the form of the base, a pharmaceutically acceptable salt, a solvate or a hydrate, and optionally in combination with at least one pharmaceutically acceptable excipient. Said excipients are selected according to the pharmaceutical form and the desired method of administration from among the customary excipients, which are known to the skilled worker.

In the pharmaceutical compositions of the invention for oral, sublingual, subcutaneous, intramuscular, intravenous, topical, local, intratracheal, intranasal, transdermal, rectal, or intraocular administration, the active principle of general formula (I) above, or its salt, solvate or hydrate where appropriate, may be administered in unit administration form, as a mixture with at least one conventional pharmaceutical excipient, to animals and to human beings for the prophylaxis or treatment of the above disorders and diseases.

The unit administration forms may be, for example, tablets, gel capsules, granules, powders, oral or injectable solutions or suspensions, transdermal patches, forms for administration sublingually, buccally, intratracheally, intraocularly, intranasally or by inhalation, topical, transdermal, subcutaneous, intramuscular or intravenous administration forms, rectal administration forms or implants. For topical administration consideration may be given to creams, gels, ointments, lotions or eyewashes.

These pharmaceutical forms are prepared in accordance with the methods that are customary in the fields in question.

Said unit forms are dosed so as to allow daily administration of from 0.001 to 20 mg of active principle per kg of body weight, depending on the pharmaceutical form.

There may be specific cases in which higher or lower doses are appropriate; such dosages are not outside the scope of the invention. In accordance with common practice, the dosage appropriate to each patient is determined by the clinician in accordance with the method of administration, the weight and the response of said patient.

The present invention according to another of its aspects also provides a method of treating the pathologies indicated above which comprises administering to a patient an effective dose of a compound according to the invention or one of its pharmaceutically acceptable salts or hydrates or solvates.

What is claimed is:

1. A method of treating a disease in a patient, said disease selected from the group consisting of peripheral neuropathy, and Parkinson's disease, comprising administering to said patient an effective amount of a compound of formula (I) or a pharmaceutically acceptable salt thereof:

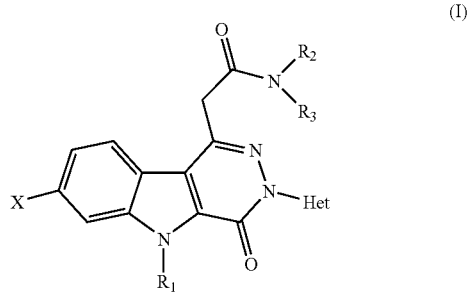

in which

X represents a hydrogen or halogen atom, $R_1$ represents a hydrogen atom or a ($C_1$-$C_4$)alkyl group, $R_2$ and $R_3$ each independently of one another represent a hydrogen atom or a ($C_1$-$C_4$)alkyl group, or else $R_2$ and $R_3$, together with the nitrogen atom bearing them, form a pyrrolidinyl, piperidinyl, morpholinyl or 4-($C_1$-$C_4$)alkylpiperazinyl group, and Het represents a heteroaromatic group of pyridinyl, quinolinyl, isoquinolinyl, pyrimidinyl, pyrazinyl or pyridazinyl type which may carry one or more halogen atoms and/or one or more ($C_1$-$C_4$)alkyl and/or ($C_1$-$C_4$)alkoxy groups.

2. The method according to claim 1, wherein X represents a halogen atom.

3. The method according to claim 1, wherein $R_1$ represents a ($C_1$-$C_4$)alkyl.

4. The method according to claim 1, wherein $R_2$ and $R_3$, each independently of one another, represent a ($C_1$-$C_4$)alkyl group or else $R_2$ and $R_3$, together with the nitrogen atom bearing them, form a pyrrolidinyl or 4-($C_1$-$C_4$)alkylpiperazinyl group.

5. The method according to claim 1, wherein Het represents a heteroaromatic group of pyridinyl type which may carry one or more halogen atoms and/or one or more ($C_1$-$C_4$)alkyl and/or ($C_1$-$C_4$)alkoxy groups.

6. The method according to claim 1, wherein X represents a chlorine atom and $R_1$ represents a methyl group.

7. The method according to claim 1, wherein the disease is peripheral neuropathy.

8. The method according to claim 1, wherein the disease is Parkinson's disease.

9. The method according to claim 2, wherein the disease is peripheral neuropathy.

10. The method according to claim 2, wherein the disease is Parkinson's disease.

11. The method according to claim 3, wherein the disease is peripheral neuropathy.

12. The method according to claim 3, wherein the disease is Parkinson's disease.

13. The method according to claim 4, wherein the disease is peripheral neuropathy.

14. The method according to claim 4, wherein the disease is Parkinson's disease.

15. The method according to claim 5, wherein the disease is peripheral neuropathy.

16. The method according to claim 5, wherein the disease is Parkinson's disease.

17. The method according to claim 6, wherein the disease is peripheral neuropathy.

18. The method according to claim 6, wherein the disease is Parkinson's disease.

* * * * *